United States Patent
Woelfel et al.

(10) Patent No.: US 11,476,013 B2
(45) Date of Patent: Oct. 18, 2022

(54) ANTI-SCATTER COLLIMATOR AND METHOD FOR PRODUCING AN ANTI-SCATTER COLLIMATOR

(71) Applicant: Siemens Healthcare GmbH, Erlangen (DE)

(72) Inventors: Stefan Woelfel, Dormitz (DE); Michael Teuber, Forchheim (DE); Nick Dinkel, Forchheim (DE); Barbara Hintz, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/183,661

(22) Filed: Feb. 24, 2021

(65) Prior Publication Data
US 2021/0280335 A1 Sep. 9, 2021

(30) Foreign Application Priority Data
Mar. 5, 2020 (DE) ...................... 10 2020 202 855.9

(51) Int. Cl.
*G21K 1/02* (2006.01)
*A61B 6/00* (2006.01)
*A61B 6/06* (2006.01)
*G01T 1/161* (2006.01)

(52) U.S. Cl.
CPC ............... *G21K 1/025* (2013.01); *A61B 6/06* (2013.01); *A61B 6/4208* (2013.01); *G01T 1/161* (2013.01)

(58) Field of Classification Search
CPC ........ G21K 1/025; A61B 6/06; A61B 6/4241; A61B 6/032; A61B 6/4208; G21F 1/00; G01T 1/161; G01T 1/20; G01N 23/046
See application file for complete search history.

(56) References Cited

U.S. PATENT DOCUMENTS

| | | | |
|---|---|---|---|
| 4,731,534 A | 3/1988 | Klein et al. | |
| 5,949,850 A * | 9/1999 | Tang | G03F 7/0007 378/154 |
| 2003/0021379 A1 | 1/2003 | Klotz et al. | |
| 2005/0029462 A1 | 2/2005 | Lyons et al. | |

(Continued)

FOREIGN PATENT DOCUMENTS

| | | |
|---|---|---|
| CN | 1407333 A | 4/2003 |
| CN | 1593344 A | 3/2005 |

(Continued)

OTHER PUBLICATIONS

German Office Action and English translation thereof dated Nov. 2, 2020.

(Continued)

*Primary Examiner* — Don K Wong
(74) *Attorney, Agent, or Firm* — Harness, Dickey & Pierce, P.L.C.

(57) ABSTRACT

An anti-scatter collimator is for arrangement in a stacked construction with an X-ray detector. In an embodiment, the anti-scatter collimator includes collimator walls arranged adjacently at least along a first direction. The collimator walls are mutually spaced to provide a through-channel between each pair of adjacent collimator walls. The through-channels provided by the arrangement of the multiplicity of collimator walls are at least partially filled with a filler material.

13 Claims, 4 Drawing Sheets

(56) References Cited

U.S. PATENT DOCUMENTS

| | | |
|---|---|---|
| 2005/0053188 A1 | 3/2005 | Gohno |
| 2013/0121475 A1 | 5/2013 | Deych et al. |
| 2014/0042333 A1 | 2/2014 | Niederlohner et al. |
| 2015/0030120 A1 | 1/2015 | Ergler et al. |
| 2019/0388043 A1 | 12/2019 | Freund et al. |

FOREIGN PATENT DOCUMENTS

| | | |
|---|---|---|
| CN | 103584873 A | 2/2014 |
| CN | 110613474 A | 12/2019 |
| DE | 102005028413 A1 | 12/2006 |
| DE | 102013214684 A1 | 1/2015 |
| JP | 2009232955 A | 10/2009 |

OTHER PUBLICATIONS

German Decision to Grant and English translation thereof dated Jul. 12, 2021.
German Office Action dated Feb. 11, 2020.

\* cited by examiner

ANTI-SCATTER COLLIMATOR AND METHOD FOR PRODUCING AN ANTI-SCATTER COLLIMATOR

PRIORITY STATEMENT

The present application hereby claims priority under 35 U.S.C. § 119 to German patent application number DE 102020202855.9 filed Mar. 5, 2020, the entire contents of which are hereby incorporated herein by reference.

FIELD

Example embodiments of the application generally relate to an anti-scatter collimator for arranging in a stacked construction with an X-ray detector, to an X-ray detector apparatus and to a medical imaging device comprising an anti-scatter collimator, and to a method for producing an anti-scatter collimator.

BACKGROUND

Medical imaging apparatuses usually comprise an X-ray source and an X-ray detector opposite. In a computed tomography system (CT system) in particular, the X-ray source and the X-ray detector are located on a diametrically opposed gantry. During a scan of an object to be imaged, for instance a patient, the object is positioned in an examination region of the computed tomography system, and the X-ray source and X-ray detector rotate around the object while the X-ray source emits X-ray radiation. The X-ray radiation that passes through the object is detected by one or more detector elements, also called detector pixels or pixel elements, of the X-ray detector, and generates a measurement signal on the basis of the locally detected X-ray radiation. Properties of the object can be inferred from the interaction, and in particular attenuation, of the X-ray radiation as it passes through the object.

X-ray detectors are equipped with anti-scatter collimators to suppress the scattered radiation produced during an acquisition. Modern computed tomography systems are equipped in particular with 3D collimators as the anti-scatter collimator, which essentially have a grid structure. These 3D collimators allow suppression of the scattered radiation in the radial direction (p direction, direction of rotation) and in the axial direction (feed direction, perpendicular to the direction of rotation). In simpler implementations, anti-scatter collimators can also be used that provide collimator walls solely along the axial direction.

SUMMARY

Anti-scatter collimators are usually positioned relative to the pixel elements of the associated X-ray detector. The inventors have discovered that changes in the position or the structures of the anti-scatter collimator, for instance caused by the forces acting on the anti-scatter collimator during operation of a medical imaging device, that affect their positioning relative to the X-ray detector can have unwanted effects and result in reduced image quality.

At least one embodiment of the application is directed to an improved anti-scatter collimator for arranging in a stacked construction with an X-ray detector, to define an X-ray detector apparatus comprising an anti-scatter collimator, and a medical imaging apparatus and a method for producing an improved anti-scatter collimator.

The claims and the description below present further advantageous embodiments and developments of the invention, some of which are inventive in their own right.

At least one embodiment of the invention relates to an anti-scatter collimator for arranging in a stacked construction with an X-ray detector, which collimator comprises collimator walls arranged adjacently at least along a first direction, wherein the collimator walls are mutually spaced such that a through-channel is provided between each pair of adjacent collimator walls, and wherein the through-channels provided by the arrangement of the multiplicity of collimator walls are at least partially filled with a filler material.

At least one embodiment of the invention also relates to an X-ray detector apparatus comprising an X-ray detector and an anti-scatter collimator according to at least one embodiment of the invention in a stacked construction, wherein the anti-scatter collimator is arranged in front of the X-ray detector in the direction of a direction of incidence of radiation for the purpose of reducing scattered radiation incident on the X-ray detector during illumination of the X-ray detector apparatus with X-ray radiation.

At least one embodiment of the invention also relates to a medical imaging device comprising an X-ray detector apparatus which comprises an X-ray detector and an anti-scatter collimator according to at least one embodiment of the invention in a stacked construction and an X-ray source arranged opposite thereto, which source is designed to illuminate the X-ray detector apparatus with X-ray radiation for the purpose of producing X-ray image datasets.

At least one embodiment of the invention also relates to a method for producing an anti-scatter collimator for arranging in a stacked construction with an X-ray detector, which method comprises the steps:

providing an arrangement of collimator walls arranged adjacently along a first direction, wherein the collimator walls are mutually spaced such that a through-channel is provided between each pair of adjacent collimator walls;

at least partially filling with a filler material the through-channels provided by the arrangement of the multiplicity of collimator walls; and hardening the filler material in the through-channels.

At least one embodiment of the invention also relates to an anti-scatter collimator for arranging in a stacked construction with an X-ray detector, comprising:

collimator walls arranged adjacently at least along a first direction, the collimator walls being mutually spaced to provide a plurality of through-channels, a through-channel of the plurality of through-channels being provided between each pair of adjacent collimator walls, and the plurality of through-channels being at least partially filled with a filler material.

At least one embodiment of the invention also relates to an X-ray detector apparatus, comprising:

an X-ray detector; and the anti-scatter collimator of an embodiment, the X-ray detector and the anti-scatter collimator being arranged in a stacked construction, the anti-scatter collimator being arranged in front of the X-ray detector in a direction of incidence of radiation to reduce scattered radiation incident on the X-ray detector during illumination of the X-ray detector apparatus with X-ray radiation.

At least one embodiment of the invention also relates to a medical imaging device, comprising:

the X-ray detector apparatus of an embodiment; and an X-ray source, arranged opposite of the X-ray detector apparatus, the X-ray source being designed to illuminate the X-ray detector apparatus with X-ray radiation for to produce X-ray image datasets.

At least one embodiment of the invention also relates to a method for producing an anti-scatter collimator for arrangement in a stacked construction with an X-ray detector, the method comprising:

providing an arrangement of collimator walls arranged adjacently along a first direction, to provide a plurality of through-channels, a through-channel of the plurality of through-channels being provided between each pair of adjacent collimator walls;

at least partially filling the plurality of through-channels, provided by the arrangement of the multiplicity of collimator walls, with a filler material; and hardening the filler material in the plurality of through-channels.

BRIEF DESCRIPTION OF THE DRAWINGS

The invention is described below using example embodiments with reference to the accompanying figures. Schematic, highly simplified diagrams that are not necessarily to scale appear in the figures, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an anti-scatter collimator for arranging in a stacked construction with an X-ray detector, which collimator comprises collimator walls arranged adjacently at least along a first direction, wherein the collimator walls are mutually spaced such that a through-channel is provided between each pair of adjacent collimator walls, and wherein the through-channels provided by the arrangement of the multiplicity of collimator walls are at least partially filled with a filler material.

The first direction can run in particular perpendicular to the stacking direction when the anti-scatter collimator is in the stacked assembly with an X-ray detector. The stacking direction can run substantially parallel to a direction of incidence of X-ray radiation for illuminating the X-ray detector.

The collimator walls are designed or oriented to be substantially parallel to the stacking direction and are adjacently arranged along the first direction, wherein a deviation of the parallel orientation from the stacking direction can include up to 10 degrees, in particular less than 5 degrees, from the stacking direction. This can include the possibility that the collimator walls are oriented at a slightly inclined angle onto a focal point of an X-ray source arranged for illuminating the X-ray detector. Consequently, the through-channels are also likewise oriented substantially parallel to the stacking direction. The orientation along the stacking direction allows the X-ray radiation from the direction of incidence of radiation to pass through the anti-scatter collimator, whereas X-ray radiation scattered out of the direction of incidence of radiation, which may have a negative impact on the image quality, can be absorbed by the collimator walls. The direction of incidence of radiation can here describe essentially the direction of propagation of the X-ray radiation emitted by an X-ray source towards the X-ray detector for the purpose of illuminating the X-ray detector.

In the stacked assembly, a through-channel can be associated with a pixel element of the X-ray detector. A through-channel may also be associated with a group of pixel elements. In particular, it is possible during production of the stacked assembly to align the collimator walls relative to the X-ray detector or to the pixel elements of the X-ray detector.

The collimator walls are designed according to at least one embodiment of the invention to be at least adjacent to one another along the first direction. If the collimator walls are designed solely to be adjacent along the first direction, the anti-scatter collimator can be essentially in the form of a lamellar structure. Through-channels between the collimator walls and bounded by the collimator walls are then bounded solely on two sides along the first direction. In addition, however, in other embodiment variants, the anti-scatter collimator can have collimator walls that are designed to be adjacent also perpendicular to the first direction. This means, according to a preferred embodiment variant of the anti-scatter collimator, that collimator walls can also be formed in a second direction, which is perpendicular to the first direction and to the stacking direction, with the result that the anti-scatter collimator has a two-dimensional grid-like structure in a horizontal section along the first and second directions. In this case, the through-channels defined by the collimator walls are consequently bounded by collimator walls both in the first direction and in the second direction. A collimator of this type may also be referred to as a 3D collimator.

The collimator walls can comprise in particular a material that absorbs X-ray radiation strongly. The collimator walls preferably comprise tungsten. The plurality of collimator walls may also comprise, however, lead, molybdenum, zinc or another material whose absorption performance with regard to X-ray radiation results in sufficiently high suppression of the scattered radiation.

The filler material preferably comprises a material having a lower coefficient of absorption than the material of the collimator walls. In advantageous embodiments, the filler material absorbs less than 5 percent, preferably less than 3%, of an amount of image-producing radiation. The filler material can preferably be substantially transparent to X-ray radiation, where this can include an absorption by the filler material of up to 5 percent. The amount of image-producing radiation can denote the amount of radiation which, in particular after passing through the anti-scatter collimator without stiffener, can be incident on the detection surface of the detector element or can be detected by the detector element.

The filler material may be based, for example, on an epoxy resin, an acrylic resin or another potting compound or adhesive material.

The filler material in the through-channels can advantageously ensure greater mechanical stability of the anti-scatter collimator without significantly impairing the image quality or the dose efficiency.

The inventor has found that the filler material in the through-channels can advantageously increase the stiffness and strength of the anti-scatter collimator during operation. Increased mechanical stability of the anti-scatter collimator can advantageously be achieved. It is advantageously possible to reduce deformation of the anti-scatter collimator caused by forces acting during operation of a medical imaging device. In particular, deformation of the anti-scatter collimator caused by rotation-induced centrifugal forces acting in a CT system can be reduced to less than 100 μm, for instance to less than 30 μm. The anti-scatter collimator advantageously can be more stable under the influence of the rotational forces.

Sufficient mechanical stability of the anti-scatter collimator can advantageously be achieved without the anti-scatter collimator being mechanically joined directly to a converter unit of an X-ray detector, for instance by direct adhesion. This can be especially advantageous in the case of a direct-converting X-ray detector, for instance, because the direct-converting converter element may have poor strength properties.

An additional advantage can be providing an improved anti-scatter collimator in a more cost-effective manner since no further stabilizing elements, for instance stiffening plates or the like, have to be provided and connected to the anti-scatter collimator.

In a further embodiment of the anti-scatter collimator, the collimator walls have a wall height perpendicular to the first direction and in the direction of a direction of incidence of radiation, wherein an effective fill height of the filler material in the direction of incidence of radiation in the through-channels is less than the wall height.

In this context, the effective fill height of the filler material can define the summed total height of the filler material inside a through-channel along the direction of incidence of radiation.

A lower effective fill height results in advantageously lower absorption. The effective fill height is then selected in particular to achieve sufficiently high stability during use of the anti-scatter collimator. Depending on the use of the anti-scatter collimator, i.e. for instance depending on the medical imaging device, and depending on the design of the anti-scatter collimator, for instance the extent of the anti-scatter collimator along the first and/or second direction, different fill heights can be sufficient to ensure sufficient stability. Advantageously, the ratio of strength and X-ray radiation absorption can be selected optimally by the fill height, so that a desired stability can be achieved at the same time as low absorption.

According to an advantageous embodiment variant, the effective fill height comprises less than half the wall height, more preferably less than a third of the wall height. For example, the effective fill height can comprise at least 1 mm. The effective fill height preferably comprises more than 1 mm, for instance at least 2 mm.

According to an advantageous embodiment variant, the effective fill height is substantially the same for all the through-channels of the anti-scatter collimator. This means that in advantageous embodiments, the fill height is substantially constant over the extent of the anti-scatter collimator along the first direction and the second direction. It is advantageously possible to achieve uniform control of the amount of radiation over the extent of the anti-scatter collimator, or in particular for all the through-channels.

The anti-scatter collimator can have a beam exit side and a beam entry side, which lies opposite in a direction of incidence of radiation. The beam entry side of the anti-scatter collimator can be formed on the side of the anti-scatter collimator that, in a stacked assembly with an X-ray detector, is further away from the X-ray detector. While the anti-scatter collimator is in use, the beam entry side is nearer an X-ray source for illuminating the X-ray detector. The beam entry side of the anti-scatter collimator can be formed on that side of the anti-scatter collimator that, in a stacked assembly with an X-ray detector, is nearer the X-ray detector. While the anti-scatter collimator is in use, the beam exit side is then further away from an X-ray source for illuminating the X-ray detector.

The beam exit side and the beam entry side are substantially planar in form along the first and second directions and perpendicular to the direction of incidence of radiation.

In an embodiment variant of the scattered radiation detector, the through-channels are filled with the filler material in a subregion that adjoins the beam exit side or in a subregion that adjoins the beam entry side.

The through-channels can each be filled up to the effective fill height in a subregion adjoining the beam entry side or beam exit side. A stable anti-scatter collimator can advantageously be provided.

Subregions that adjoin the beam exit side or beam entry side can advantageously be post-filled with filler material particularly easily after provision of an arrangement of collimator walls. The anti-scatter collimator can advantageously be provided particularly easily.

In addition, both a subregion adjoining the beam exit side and a subregion adjoining the beam entry side can be filled with the filler material.

The subregions can each be filled up to a partial height of the effective fill height so that the partial height of the subregion adjoining the beam exit side and the partial height of the subregion adjoining the beam entry side total to give the effective fill height. The partial height can be chosen to be the same on both sides. For example, the subregions each have at least a partial height of 1 mm. The partial height of the subregion adjoining the beam exit side and the partial height of the subregion adjoining the beam entry side can also be chosen to be different, however.

Filling up to a partial height that is less than the effective fill height in each case can advantageously simplify a filling process. Filling the anti-scatter collimator on both sides can advantageously further increase the stability of the anti-scatter collimator. This can also result in advantageously being able to use a lower effective fill height, i.e. less filler material, than for one-sided filling, with the associated potential for lower absorption in the through-channels and cost savings. In addition, the opportunity to select different partial heights on each side can be exploited to improve the ability to optimize the stability and stiffness of the anti-scatter collimator. Furthermore, dual-sided filling and an associated closure of the mouths of the through-channels reduce a contamination risk.

Alternatively, there may also be embodiments of the anti-scatter collimator in which the through-channels are filled with the filler material in a subregion of the through-channels that is central along the direction of incidence of radiation, wherein the central subregion is spaced both from the beam exit side and from the beam entry side.

It is again possible in this case to use less material to achieve an improved stability that can reduce deformations of the anti-scatter collimator over the extent of the anti-scatter collimator in a uniform manner.

In an advantageous embodiment variant of the anti-scatter collimator, the filler material comprises a hardenable filler material.

The filler material can be provided in particular in a first state, which is flowable or at least malleable, and in order to provide the anti-scatter collimator can be hardened once the through-channels have been filled with the filler material.

For example, the filler material in a first state, which is flowable or at least malleable, can have a viscosity between 0.4 mPa s and 106 mPa s. The appropriate viscosity to be provided for filling may depend, however, on the filling process that is used to fill the through-channels of the anti-scatter collimator. The method employed for hardening the filler material usually depends on the filler material used. For example, the filler material after hardening has a stiffness of at least 1000 MPa, preferably at least 3000 MPa. The stiffness (modulus of elasticity) can be measured by a method given by DIN ISO EN 527-1, for instance.

The filler material may comprise, for example, an epoxy resin, an acrylic resin or another hardenable adhesive material or potting compound, for instance a UV-hardenable adhesive. A potting compound such as employed for preparing polished samples or potted electronic components can be used, for example, as the filler material.

A filler material based on epoxy resin can advantageously exhibit very low shrinkage during hardening and particularly good adhesion to the collimator walls. A filler material based on acrylic resin can, in addition to exhibiting very low shrinkage, advantageously be easy to handle and have short hardening times.

Cost-effective and easily available filler materials can advantageously be used to provide improved stability, which materials can also provide a high degree of stiffening while ensuring relatively low absorption.

The hardened material in the through-channels ensures improved stiffness of the anti-scatter collimator. The possibility of providing in a fluid or at least malleable state before hardening allows the filler material to be introduced into the through-channels and hence to fill the through-channels. In particular, this is also possible after providing the arrangement of collimator walls, and therefore existing anti-scatter collimators and processes for producing anti-scatter collimators can be used easily and cost-effectively.

According to a further variant of at least one embodiment of the anti-scatter collimator, the filler material comprises an optically reflective material.

An optically reflective material may comprise optically reflective pigments, for example. The optically reflective material preferably has a low coefficient of absorption. For example, the filler material can comprise titanium oxide. Another example of a possible pigment may comprise barium sulfate. There can also be other possible materials as well.

An optically reflective material can comprise in particular a material that reflects optical light. Introducing an optically reflective material into the filler material, in particular in combination with filling in a subregion that adjoins a beam exit side, can constitute a particularly advantageous embodiment variant. An optically reflective beam exit side can be achieved in this manner. This can be employed advantageously if additional illumination of a converter unit by an external light source is intended to be used for signal stabilization of the X-ray detector, as is used in some direct-converting X-ray detectors. A filler material comprising an optically reflective material can be used for uniform illumination of the converter unit, while at the same time making it possible to dispense with mounting additional reflectors, for instance by gluing onto the anti-scatter collimator. A stable anti-scatter collimator having fewer components can be provided advantageously in a cost-effective and production-efficient manner.

An alternative or additional option for providing an optically reflective beam exit side of the anti-scatter collimator can include providing inhomogeneities on the filler-material surface that adjoins the beam exit side. Inhomogeneities can comprise bubbles occurring on the surface, or a roughened surface of the filler material, with the result that optical light striking the surface can be scattered at the inhomogeneities.

At least one embodiment of the invention also relates to an X-ray detector apparatus comprising an X-ray detector and an anti-scatter collimator according to at least one embodiment of the invention in a stacked construction, wherein the anti-scatter collimator is arranged in front of the X-ray detector in the direction of a direction of incidence of radiation for the purpose of reducing scattered radiation incident on the X-ray detector during illumination of the X-ray detector apparatus with X-ray radiation.

The X-ray detector may be a direct-converting or an indirect-converting X-ray detector.

In direct-converting X-ray detector apparatuses, the X-ray radiation or the photons can be converted into electrical pulses by a suitable converter material. Examples of materials that can be used as the converter material are CdTe, CZT, CdZnTeSe, CdTeSe, CdMnTe, InP, $TlBr_2$, $HgI_2$, GaAs or other materials. The electrical pulses are evaluated by electronic circuits of an analysis unit, for instance in the form of an integrated circuit (Application Specific Integrated Circuit, ASIC). In counting X-ray detector apparatuses, incident X-ray radiation can be measured by counting the electrical pulses triggered by the absorption of X-ray photons in the converter material. In addition, the height of the electrical pulse is usually proportional to the energy of the absorbed X-ray photon. Spectral information can hence be extracted by comparing the height of the electrical pulse with a threshold value.

In indirect-converting X-ray detector apparatuses, the X-ray radiation or the photons can be converted into light by a suitable converter material and into electrical pulses by optically coupled photodiodes. Scintillators, for instance GOS ($Gd2O2S$), CsJ, YGO or LuTAG, are often used as the converter material. In addition, the generated electrical signals are processed, read out and then forwarded to a processing unit by means of an analysis unit comprising electronic circuits.

The X-ray detector can comprise a multiplicity of pixel elements arranged as an array for spatially resolved measurement of the incident X-ray radiation. The position of the anti-scatter collimator, in particular of the through-channels and of the collimator walls, can be aligned relative to the array of the multiplicity of pixel elements. For instance, each pixel element or each group of pixel elements can be assigned a collimator wall. For example, a collimator wall can be arranged between each pair of adjacent pixel elements or between each adjacent group of pixel elements, for instance macro-pixels. An arrangement is preferably made such that a collimator wall conceals as little as possible of a sensitive surface of a pixel element in order to be able to avoid any degradation in the dose efficiency. It is also conceivable in embodiment variants that collimator walls are arranged entirely or partially above the detection surface of a pixel element, which surface is sensitive to X-ray radiation.

In particular, changes in the relative arrangement of the collimator walls, or the through-channels, and the pixel elements as a result of, or during, operation, can have negative impacts on the quality of the information obtained by the X-ray detector apparatus, in particular on the image quality. This can include an unintentional displacement of the collimator walls out of a relative position between two adjacent pixel elements and hence unintentional shadowing of a sensitive surface of a pixel element, or even time-varying shadowing by the collimator walls during operation.

Such changes may be caused by mechanical deformation or flexing of the anti-scatter collimator as a result of the forces acting during operation of a medical imaging device.

The anti-scatter collimator according to the invention advantageously has improved stability and stiffness while at the same time being provided cost-effectively, which can counteract in particular deformations of the anti-scatter collimator resulting from forces acting during operation of the X-ray detector apparatus.

At least one embodiment of the invention also relates to a medical imaging device comprising an X-ray detector apparatus which comprises an X-ray detector and an anti-scatter collimator according to at least one embodiment of the invention in a stacked construction and an X-ray source arranged opposite thereto, which source is designed to illuminate the X-ray detector apparatus with X-ray radiation for the purpose of producing X-ray image datasets.

Then for the purpose of acquiring the X-ray image dataset, the object to be imaged can be positioned in particular between the X-ray source and the photon-counting X-ray detector, and the X-ray source can beam radiation through the object.

In particular, the medical imaging device can be in the form of a computed tomography system. It may also be in the form of a C-arm X-ray device and/or DynaCT, however, or else have a different design.

All the embodiment variants that have been described above in the context of the anti-scatter collimator according to embodiments of the invention can also be implemented correspondingly in the X-ray detector apparatus or in the medical imaging device. The description relating to the anti-scatter collimator and the aforementioned advantages of the anti-scatter collimator can accordingly be applied also to the X-ray detector apparatus according to embodiments of the invention and to the medical imaging device according to embodiments of the invention.

It is especially advantageous to use the improved anti-scatter collimator in particular in the case of a CT system in which high centrifugal forces may act on the anti-scatter collimator because of the rotation of the X-ray detector/X-ray source assembly.

At least one embodiment of the invention also relates to a method for producing an anti-scatter collimator for arranging in a stacked construction with an X-ray detector, which method comprises the steps:

providing an arrangement of collimator walls arranged adjacently along a first direction, wherein the collimator walls are mutually spaced such that a through-channel is provided between each pair of adjacent collimator walls;

at least partially filling with a filler material the through-channels provided by the arrangement of the multiplicity of collimator walls; and hardening the filler material in the through-channels.

The collimator walls and accordingly the arrangement of the multiplicity of collimator walls can be provided, for example, by means of a screen-printing process, an additive production process, for instance an SLM process (selective laser melting), a primary-shaping process using a metal-filled plastic material or produced in another way, and provided for the step of filling. The arrangement of collimator walls arranged adjacently along a first direction is then provided in particular unfilled in the step of providing.

In the step of at least partially filling, the filler material may be provided in particular in a flowable or at least malleable state, and the through-channels can be filled with the filler material. The at least partially filling can comprise filling the through-channels with the filler material in a subregion that adjoins the beam exit side, and/or in a subregion that adjoins the beam entry side. The at least partially filling can comprise filling a central subregion. In particular, the through-channels are filled up to an effective fill height.

The filler material preferably comprises a material that can be provided for filling in a flowable or at least malleable state. For example, the filler material in a first state, which is flowable or at least malleable, can have a viscosity in a range between 10-1 mPa s and 106 mPa s. The viscosity can be measured by a Brookfield rotational viscometer, for instance. The appropriate viscosity to be provided for filling may depend in particular, however, on the filling process that is used to fill the through-channels of the anti-scatter collimator.

The method also comprises a step of hardening the filler material. In the hardening step, the previously flowable or at least malleable filler material can be hardened into a rigid state, making it possible to achieve stiffening of the arrangement of the multiplicity of collimator walls. Improved stability of the anti-scatter collimator can hence be achieved. The method employed for hardening the filler material may depend in particular on the filler material used.

For a UV-hardenable adhesive, the hardening may require exposure to UV light, for instance. The hardening of epoxy resins and acrylic resins can be based on a chemical polymerization reaction. These may be cured, and hence hardened, at room temperature for example by means of an applied or added hardener or by thermal self-curing. In this case, the curing of the resins can be assisted by a moderate supply of heat below 100° C., also known as annealing. It is also possible to use thermoplastic or thermosetting filler materials. Thermoplastic filler materials, for instance potting compounds, soften at a raised temperature and harden on cooling. Thermosetting filler materials, for instance potting compounds, can be hardened at a raised temperature.

In an embodiment variant of the method, the step of at least partially filling comprises inserting the arrangement of collimator walls arranged adjacently along a first direction into a reservoir of filler material provided in a flowable or at least malleable state.

The insertion can comprise immersing or pressing the arrangement of the multiplicity of collimator walls into the reservoir.

For example, a reservoir of a flowable filler material having a low viscosity in the range 10-1 mPa s to 104 mPa s, preferably between 0.5 mPa s and 2000 mPa s, is provided. The arrangement of the multiplicity of collimator walls can then be immersed into the reservoir with little applied force. The immersion can bring about filling of the through-channels.

Filling of the through-channels can advantageously be achieved in a simple manner. Filling over a large area is advantageously easily possible.

The step of at least partially filling can also comprise using a vacuum process to fill the through-channels. In order to assist the filling process, it can be provided to evacuate the filling environment in which are arranged the reservoir and the arrangement of the multiplicity of collimator walls for filling. Reducing the pressure below atmospheric pressure in the filling environment can cause the filler material to penetrate into the through-channels up to a fill height. In particular, an easily repeatable filling process can thereby be implemented that has a defined fill height in the through-channels. In addition, a better guarantee of constant fill height in the through-channels within the multiplicity of through-channels can be achieved more easily. Furthermore, filling using a vacuum process extends the set of usable fillers, because it is also possible to use fillers that are more viscous, for instance in the region of 104 mPa s, than in the case of a pure immersion process.

When using a vacuum process for the at least partial filling, in embodiment variants it is also possible to dispense with immersing the arrangement into the reservoir or at least to reduce an immersion depth. A reservoir of a flowable filler can be provided and the arrangement can then be positioned, for instance, merely above the surface of the filler or on the surface of the filler. Evacuating the filling environment in which are arranged the reservoir and the arrangement of the multiplicity of collimator walls for filling can cause the filler material to penetrate into the through-channels up to a desired fill height. In this case, wetting the outer collimator walls with filler can be avoided.

In an alternative variant, a reservoir is provided containing a viscous or paste-like filler material of higher viscosity. For example, the filler material has a viscosity in the range 104 mPa s to 106 mPa s. The viscous filler material is applied, for instance, as a layer of specified and preferably constant layer thickness over the surface of a support.

The arrangement of the multiplicity of collimator walls can be inserted, i.e. pressed, into the reservoir, whereby the viscous filler material can be introduced into the through-channels. As a result of the higher viscosity of the filler material, this can require a higher applied force than when immersing into a more free-flowing material of lower viscosity.

In a further embodiment variant of the method, the step of at least partially filling comprises applying the filler material in a flowable or at least malleable state to the arrangement of collimator walls arranged adjacently along a first direction, and introducing the filler material into the through-channels by means of a mechanical process.

In this case, the filler material is preferably applied in a viscous or paste-like state over the surface of a beam entry side or a beam exit side of the anti-scatter collimator. The filler material preferably has a higher viscosity, for instance in the range 104 to 106 mPa s. The viscous filler material is preferably applied in a uniform layer thickness over the surface of the beam exit side and/or beam entry side.

The filler material can then be introduced mechanically, for instance pressed or pushed, into the through-channels. For example, a doctor blade can be used to introduce the filler material into the through-channels by pulling or pushing the doctor blade over the arrangement of collimator walls, with the applied filler material pressed into the through-channels in the process.

It is also conceivable that in a variant of the production method, the step of at least partially filling comprises using an application apparatus to introduce the filler material in a flowable or at least malleable state directly into the through-channels individually.

Individually can include here that each through-channel is filled separately successively in time by means of an application apparatus, for instance in the form of a cannula or dispenser needle, that can be positioned at a mouth of a through-channel or into a through-channel or inserted therein. It can also include that each through-channel of at least one group of through-channels is filled simultaneously by means of an application apparatus provided for each one. The application apparatus can be used to deliver filler material into the through-channels individually. The delivery may also include inserting the tip of a dispenser needle into a through-channel and moving it out of the through-channel as filler material is discharged by the dispenser needle.

A higher viscosity can again be used advantageously in this case to prevent flow of the introduced material. For instance, the viscosity can be at least 104 mPa s.

In addition, an application apparatus inserted into the through-channels can advantageously be used to facilitate filling even those subregions of the through-channels that are spaced apart from the beam entry side or from the beam exit side.

In the context of the invention, features described with regard to different embodiments of the invention and/or different claim categories (method, use, apparatus, system, arrangement, etc.) can also be combined to give further embodiments of the invention. For example, a claim relating to an apparatus can also be developed by combining with features described or claimed in connection with a method, and vice versa. Functional features of a method can be implemented by correspondingly designed object-related components. In addition to the embodiments of the invention described explicitly in this application, a person skilled in the art will be able to arrive at various further conceivable embodiments of the invention without departing from the scope of the invention defined by the claims.

The use of the indefinite article "a" or "an" does not rule out the possibility of there also being more than one of the feature concerned. The use of the expression "comprise" does not exclude the possibility of the terms linked by the expression "comprise" being identical. For example, the medical imaging apparatus comprises the medical imaging apparatus. The use of the expression "unit" does not exclude the possibility that the subject to which the expression "unit" relates comprises a plurality of components that are spatially separate from one another.

Figure 1:
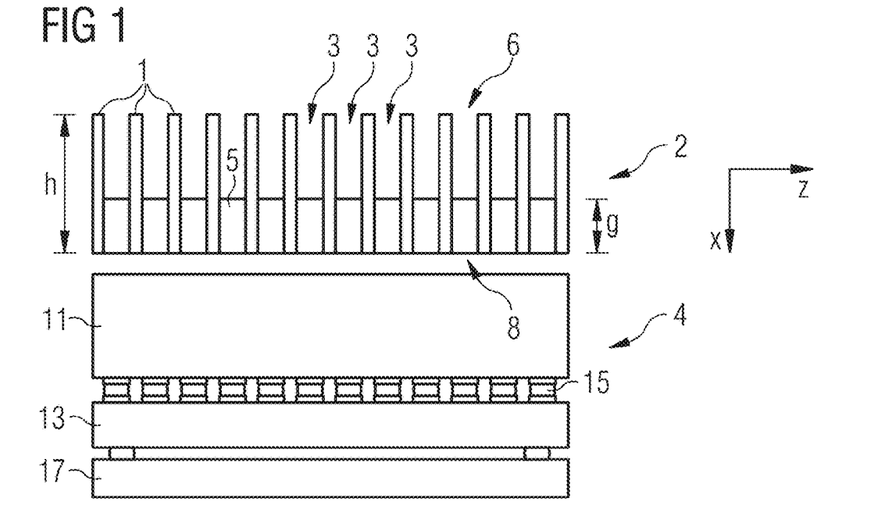
FIG. 1. is a schematic sectional diagram of an X-ray detector apparatus comprising an X-ray detector and an anti-scatter collimator in a first embodiment variant in a stacked assembly.

FIG. 1. shows a schematic sectional diagram of an X-ray detector apparatus comprising an X-ray detector 4 and an anti-scatter collimator 2 in a first embodiment variant in a stacked assembly.

The anti-scatter collimator 2 is arranged in front of the X-ray detector 4 in the direction of a direction of incidence of radiation for the purpose of reducing scattered radiation incident on the X-ray detector 4 during illumination of the X-ray detector apparatus with X-ray radiation. In the diagram shown, the direction of incidence of radiation runs substantially parallel to the x-axis.

In the stacked assembly, the anti-scatter collimator 2 has a beam entry side 6, which is nearer an X-ray source for illuminating the X-ray detector 4 and is further away from the X-ray detector 4. Then the anti-scatter collimator accordingly has, lying opposite in a direction of incidence of radiation, a beam exit side 8, which is further away from the X-ray source for illuminating the X-ray detector 4 and is nearer the X-ray detector 4. The beam entry side 6 and the beam exit side 8 can have substantially the same planar dimensions as the converter elements 11 of an X-ray detector 4 that are assigned to an associated anti-scatter collimator.

The X-ray detector 4 comprises a converter element 11 for converting incident X-ray radiation into electrical signals. In addition, the converter element 11 is coupled via electrically conductive connections 15 to an analysis unit 13, which is designed to process the electrical signals from the converter unit 11. The analysis unit can also be coupled to a readout unit 17 for collecting and reading out the processed signals or to a substrate 17. The X-ray detector can comprise in particular a multiplicity of pixel elements arranged as an array for spatially resolved measurement of the incident X-ray radiation. The X-ray detector 4 may be a direct-converting or an indirect-converting X-ray detector 4.

The anti-scatter collimator 2 comprises collimator walls 1 arranged adjacently at least along a first direction (parallel to the z-axis in the illustration), with the collimator walls 1 mutually spaced such that a through-channel 3 is provided between each pair of adjacent collimator walls 1. The through-channels 3 provided by the arrangement of the multiplicity of collimator walls 1 are partially filled with a filler material 5. The collimator walls 1 and the through-channels are oriented substantially parallel to the stacking direction, which can include that the collimator walls 1, and the through-channels 3 formed thereby, can also be oriented at a slightly inclined angle onto a focal point of an X-ray source 37 arranged for illuminating the X-ray detector 4.

Figure 2:
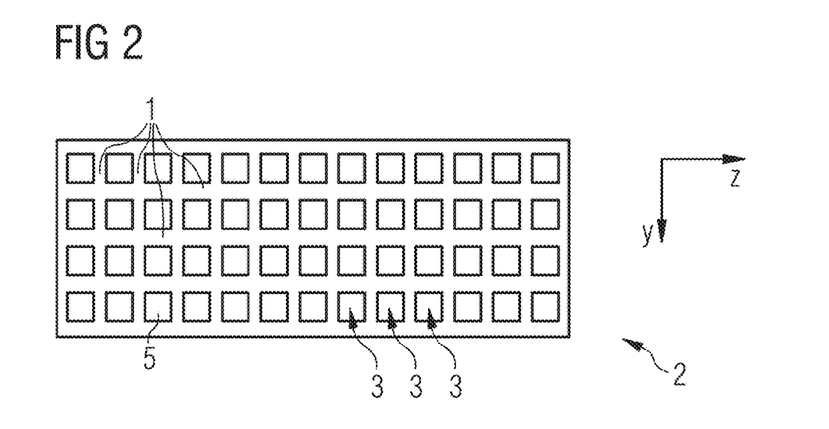
FIG. 2 is a schematic plan view of an anti-scatter collimator in a second embodiment variant.

The collimator walls 1 are designed according to the invention to be at least adjacent to one another along the first direction. The anti-scatter collimator 2 can thereby form essentially a lamellar structure. Viewed from above onto the arrangement, this can then correspond to a grating structure. According to a preferred embodiment variant of the anti-scatter collimator 2, collimator walls 1 are formed in a second direction, which is perpendicular to the first direction and to the stacking direction, with the result that the anti-scatter collimator 2 has a two-dimensional grid-like structure in a horizontal section along the first and second directions, as also illustrated in FIG. 2 in a plan view onto an anti-scatter collimator 2.

The collimator walls 1 comprise in particular a material that absorbs X-ray radiation strongly, for instance preferably tungsten.

The filler material 5 preferably comprises a material having a lower coefficient of absorption than the material of the collimator walls 1. In advantageous embodiments, the filler material 5 absorbs less than 5 percent, more preferably less than 3 percent, of an amount of image-producing radiation, and is as transparent as possible to X-ray radiation. The filler material 5 preferably comprises a hardenable material. This means it can be provided in a flowable or at least malleable state for filling the through-channels 3 and then hardened to develop the improved stiffness of the anti-scatter collimator 2.

The specific filler material 5 can depend in particular on the method used to produce the anti-scatter collimator 2. Other viscosities and material properties of the filler material can be advantageous depending on the production method. The filler material in the first state, which is flowable or at least malleable, preferably has a viscosity between 10-1 mPa s and 106 mPa s, preferably in the region of 0.5 mPa s and 8*105 mPa s. The filler material may comprise, for example, an epoxy resin (e.g. Scotch-Weld DP100, Scotch-Weld DP760 (white), Araldite 2020), an acrylic resin (e.g. ClaroCIT, Struers) or another hardenable adhesive material or potting compound, for instance a UV-hardenable adhesive (e.g. Delo photobond). A large number of alternatives are also possible in addition to the specified examples. Other potting compounds, for instance those employed for preparing polished samples or potted electronic components, can be also used as the filler material, for example. Other adhesive materials and polymers that are hardenable can also be used.

The filler material fills the through-channels at least partially. The effective fill height g of the filler material 5 is then preferably less than the wall height h of the collimator walls 1 in the direction of incidence of radiation. Lower fill heights are usually associated with a preferred lower absorption of X-ray radiation.

The effective fill height of the filler material can be defined as the summed total height of the filler material inside a through-channel along the direction of incidence of radiation. In the diagram shown in FIG. 1, the through-channels 3 are filled with the filler material only in a subregion that adjoins the beam exit side 8. In such a case, the effective fill height g is given directly by the height of the filling of the filler material 5. On the other hand, if the anti-scatter collimator 2 comprises, for example, a filling in a subregion that adjoins the beam exit side 8 and in a subregion that adjoins the beam entry side 6, then the effective fill height g now comprises the sum of the individual partial fill heights.

According to an advantageous embodiment variant, the effective fill height g comprises less than half the wall height h, more preferably less than a third of the wall height h. The effective fill height preferably comprises at least 1 mm, for instance 2 mm-7 mm.

In addition, the effective fill height is preferably, although not necessarily, designed to be the same for all the through-channels of the anti-scatter collimator in order to ensure a uniform absorption performance.

Each through-channel 3 of the anti-scatter collimator 2 can be associated with a pixel element of the X-ray detector 4. A through-channel 3 may also be associated with a group of pixel elements. During production of the stacked assembly, the through-channels 3 are preferably deliberately aligned relative to the pixel elements of the X-ray detector 4, for instance in such a way that as little as possible of the sensitive surface of a pixel element is concealed, in order to avoid any shadowing of the sensitive surface by a collimator wall.

In particular, changes in the relative arrangement of the collimator walls 1, or the through-channels 3, and the pixel elements as a result of, or during, operation, can have negative impacts on the quality of the information obtained by the X-ray detector apparatus, in particular on the image quality. Such changes may be caused by deformations or flexing of the anti-scatter collimator 2 as a result of the forces acting during operation of the X-ray detector apparatus. This can include an unintentional displacement of the collimator walls 1 out of a relative position between two adjacent pixel elements, or moreover even a position of the collimator walls that varies over time relative to the pixel elements during operation.

The anti-scatter collimator according to the invention advantageously facilitates an anti-scatter collimator 2 that is more stable in particular with regard to deformations and flexing, and which moreover can also be provided in a simpler and more cost-effective manner.

According to a further variant of the anti-scatter collimator 2, the filler material 5 comprises an optically reflective material, for instance an optically reflective pigmentation. For instance the filler material can comprise titanium oxide or barium sulfate as the optically reflective material. In particular titanium oxide has a suitably low coefficient of absorption for X-ray radiation and a high reflectance for optical light. Other materials can also be used as the optically reflective material.

By virtue of the reflective properties, the optically reflective material can advantageously assist illumination of the converter unit 11 with optical light that is employed in some X-ray detectors 4, in particular direct-converting X-ray detectors 4, for signal stabilization, and can result in uniform illumination of the converter element 11 beneath the anti-scatter collimator 2. For example, assistance can thereby be given to an external illumination source provided laterally outside the planar extent of the anti-scatter collimator 2 without it being necessary, for instance, to provide the mounting of additional reflector layers on the anti-scatter collimator 2.

The optically reflective material is preferably added to the filler material so as to be able to achieve a reflectance of at least 50%, more preferably of at least 60%. The reflectance can be measured using a spectrophotometer (Spectrophotometer LAMBDA 1050; measurement of spectral transmission+reflection (UV/VIS/NIR)), for instance. A reflectance of at least 50%, more preferably of at least 60%, is preferably achieved for a light source intended to be used in combination with the anti-scatter collimator.

Designing the filler material to comprise the reflective material is advantageous in particular in combination with filling the anti-scatter collimator at least at the beam exit side, which is nearer the X-ray detector in the stacked assembly, in order to ensure uniform illumination of the X-ray detector in combination with an external light source.

According to an alternative or additional embodiment variant, an optical reflectance can also be provided by inhomogeneities formed in particular on a surface of the filler material in the through-channels, which surface is nearer the X-ray detector. This can include a roughened surface of the filler material or the presence of bubbles on a surface of the filler material. Inhomogeneities can also produce or increase a reflectance for optical light by the filler material.

Figure 3:
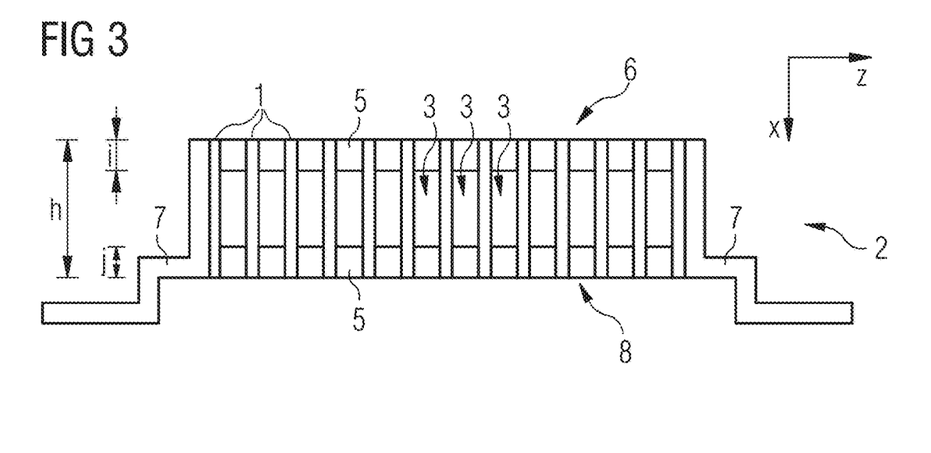
FIG. 3 is a schematic sectional diagram of an anti-scatter collimator in a third embodiment variant.

FIG. 3 shows a schematic sectional diagram of an anti-scatter collimator 2 in another embodiment variant. In this case, the anti-scatter collimator 2 is filled with the filler material 5 both in a subregion that adjoins the beam exit side 8 and in a subregion that adjoins the beam entry side 6.

The effective fill height in this variant is given by the sum of the partial height i and the partial height j.

The partial heights i, j can each comprise at least 1 mm, for example. The partial height i can be chosen to be different from the partial height j. For instance, the partial height i may comprise 1 mm and the partial height j may comprise 2 mm. Other combinations are also possible.

Alternatively, there may also be embodiments of the anti-scatter collimator 2 in which the through-channels 3 are filled with the filler material in a subregion of the through-channels 3 that is central along the direction of incidence of radiation, which central subregion is spaced both from the beam exit side 8 and from the beam entry side 6.

Regardless of any specific embodiment of the anti-scatter collimator 2, for instance filling on both sides, on one side or centrally, or a lamellar-type or grid-like design, the anti-scatter collimator 2 can also comprise a retaining element 7 for attaching the anti-scatter collimator 2.

The retaining element 7 can be used for attachment inside the X-ray detector, for instance relative to the converter element 11. The retaining element 7 can comprise a mechanical connection to the arrangement of the multiplicity of collimator walls 1 of the anti-scatter collimator 2. The retaining element 7 can be designed to span the converter element 11 in the stacked assembly in the manner of a bridge. In particular, the anti-scatter collimator, or the arrangement of the multiplicity of collimator walls 1, can be spaced apart from the converter element. In the example shown in FIG. 3, the retaining element 7 is designed for this purpose in the form of steps.

This can be advantageous in particular in those cases in which direct contact is meant to be avoided because of the material properties of the converter element 11, for instance because of low mechanical strength. Such an arrangement, however, may also increase the susceptibility to deformations. An anti-scatter collimator 2 embodied according to any of the previously described variants can nonetheless advantageously provide sufficiently high stiffness.

Figure 4:
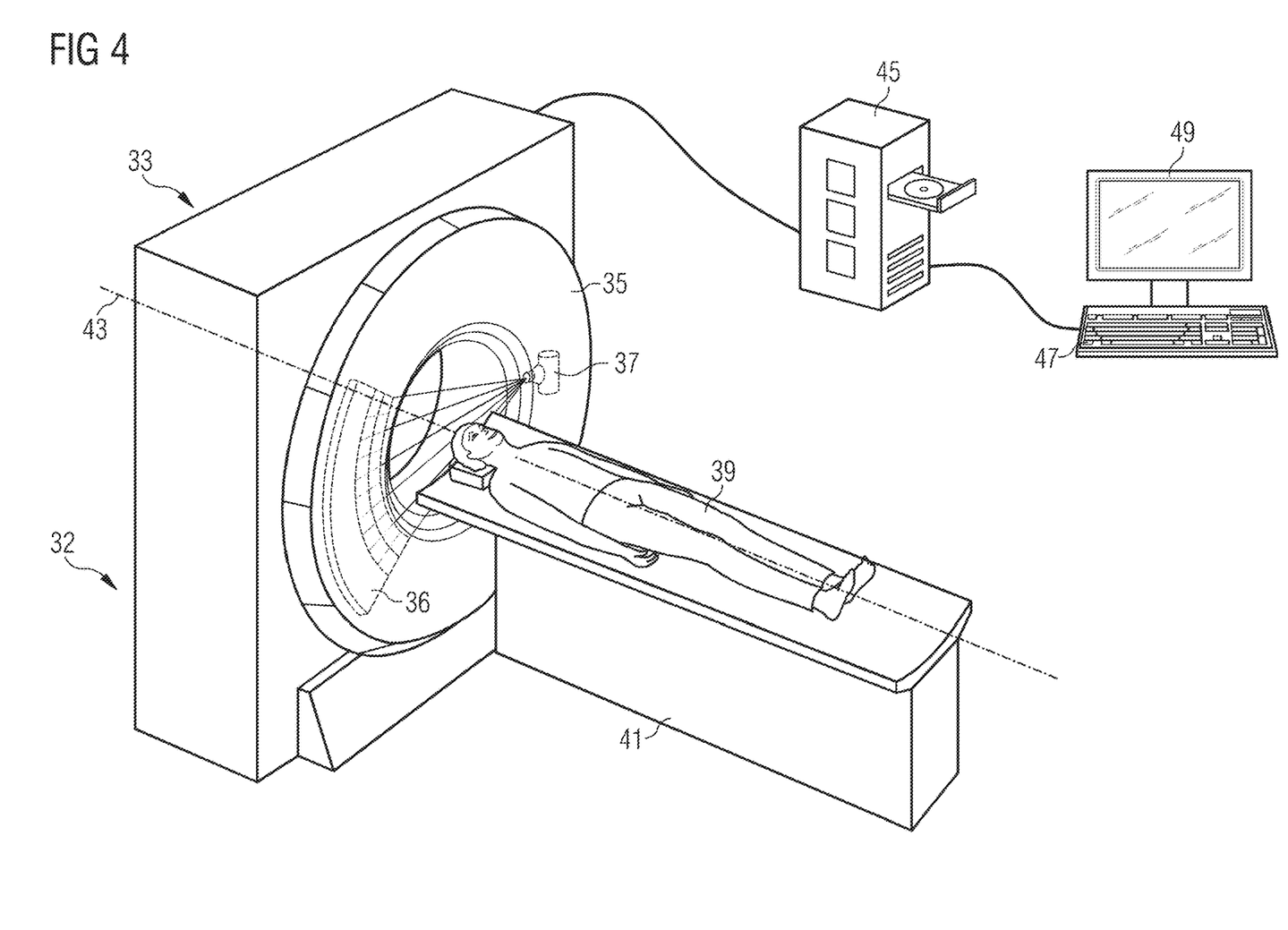
FIG. 4 is a schematic diagram of a medical imaging device.

FIG. 4 shows an example embodiment of a medical imaging device 32 in the form of a computed tomography system. The computed tomography system contains a gantry 33 having a rotor 35. The rotor 35 comprises an X-ray source 37 and the detector unit 36. The detector unit 36 comprises at least one X-ray detector apparatus according to the invention having an X-ray detector and an anti-scatter collimator in a stacked assembly. It can also comprise a plurality of X-ray detector apparatuses according to the invention. The rotor 35 can rotate about the axis of rotation 43. The object 39 under examination is supported on the patient couch 41 and can be moved along the axis of rotation z 43 by the gantry 33. A processing unit 45 is used to control the computed tomography system and to compute the sectional images. An input unit 47 and an output apparatus 49 are connected to the processing unit 45.

Figure 5:
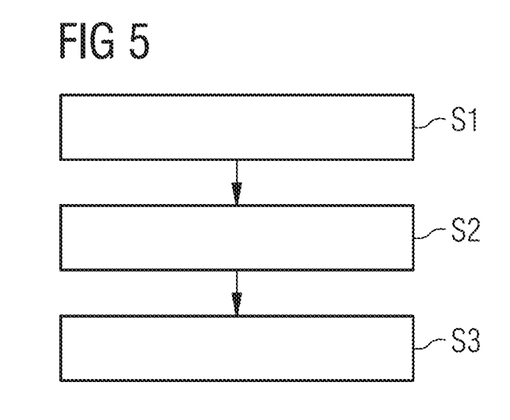
FIG. 5 is a flow diagram of an example method for producing an anti-scatter collimator.

FIG. 5 shows a flow diagram of an example method for producing an anti-scatter collimator 2.

The method comprises the steps of providing S1 an arrangement of collimator walls 1 arranged adjacently along a first direction, which collimator walls 1 are mutually spaced such that a through-channel 3 is provided between each pair of adjacent collimator walls 1. The method also comprises the step of at least partially filling S2 with a filler material 5 the through-channels 3 provided by the arrangement of the multiplicity of collimator walls 1. In addition, the method sequence shown comprises the step of hardening S3.

In the step of at least partially filling S2, the filler material 5 may be provided in particular in a flowable or at least malleable state, and the through-channels 3 can be filled with the filler material 5. In the step of hardening S3, the previously flowable or at least malleable filler material can be hardened into a rigid state, making it possible to achieve stiffening of the arrangement of the multiplicity of collimator walls 1 and providing an improved anti-scatter collimator. The hardening is chosen in particular according to the filler material used. For a UV-hardenable adhesive, the hardening may require exposure to UV light, for instance. The hardening of epoxy resins and acrylic resins can be based on a chemical polymerization reaction. These may be cured, and hence hardened, at room temperature for example by means of an applied or added hardener or by thermal self-curing. In this case, the curing of the resins can also be assisted by a moderate supply of heat below 100° C., also known as annealing. This can achieve improved stiffness in particular. For example, a filled arrangement of collimator walls is heated in an oven for several hours, for instance 2 h or 5h, to at least 50° C. and then cooled back down to room temperature. Other thermal cycles are also possible. For instance, a filled arrangement of collimator walls is heated initially for about 5 h to 50° C. and then heated for another 5 h to 70° C. It is also possible to use thermoplastic or thermosetting filler materials. Thermoplastic filler materials, for instance potting compounds, soften at a raised temperature and harden on cooling. Thermosetting filler materials, for instance potting compounds, can be hardened at a raised temperature.

Figure 6:
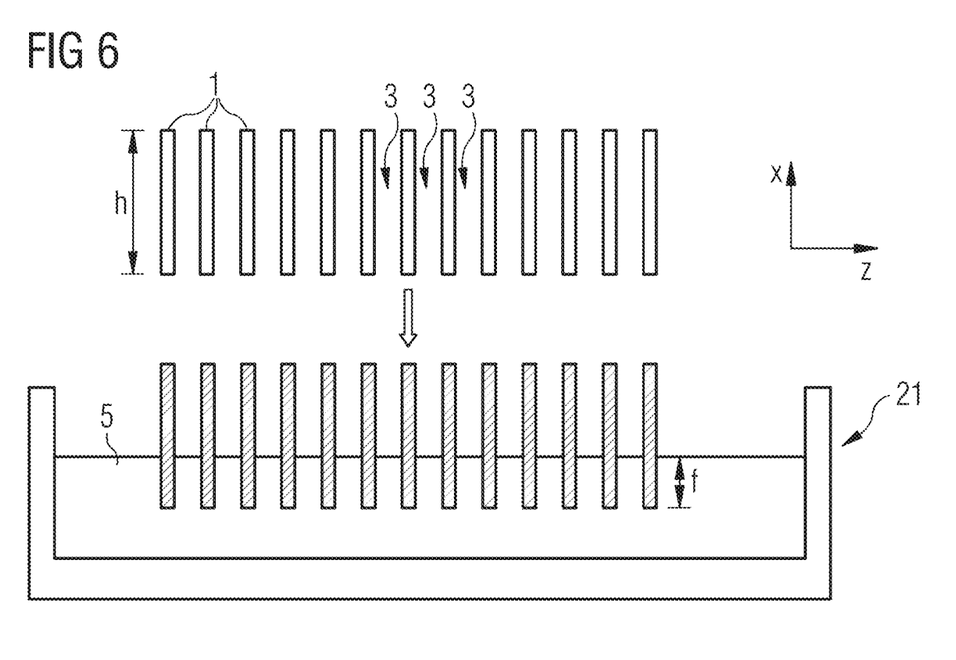
FIG. 6 is an illustration of a first embodiment variant of a method for producing an anti-scatter collimator.

FIG. 6 shows an illustration of a first embodiment variant of a method for producing an anti-scatter collimator 2.

In this method, the arrangement of the multiplicity of collimator walls 1 provided in the step of providing S1 is immersed into a reservoir 21 of filler material 5 provided in a flowable state, with the result that the through-channels 3 are filled with the filler material 5. For example, the filler material can be provided in a trough-shaped container. The arrangement containing the filled through-channels 3 can then be removed from the reservoir 21.

The step of at least partially filling S2 can comprise a vacuum process. In order to assist the filling process, it can be provided to evacuate the filling environment in which are arranged the reservoir 21 and the arrangement of the multiplicity of collimator walls for filling. Reducing the pressure below atmospheric pressure in the filling environment can cause better penetration of the filler material into the through-channels 3 up to a desired fill height g. The negative pressure required for this can depend on the viscosity of the filler material, on the duct size of the anti-scatter collimator and on the method for producing the anti-scatter collimator, which method can affect the wettability of the walls.

When using a vacuum process for the at least partial filling, in embodiment variants it is also possible to dispense with immersing the arrangement into the reservoir 21 or at least to reduce an immersion depth. A reservoir of a flowable filler 5 can be provided and the arrangement can then be positioned, for instance, merely above the surface of the filler or on the surface of the filler 5. Evacuating the filling environment in which are arranged the reservoir 21 and the arrangement of the multiplicity of collimator walls 1 for filling can cause the filler material 5 to penetrate into the through-channels 3 up to a desired fill height.

For example, filler materials of viscosities in the range 10-1 mPa s to 104 mPa s are preferably used. Specific examples of filler materials that can be used can include Araldite 2020, Scotch Weld DP 100 or a Delo photobond adhesive, for instance, as well as other options. When combined with a vacuum process, more-viscous filler materials, i.e. materials having a higher viscosity, can be used than without a vacuum process.

If filling is meant to be performed from both sides, the same procedure can also be carried out on the opposite side, and respective subregions of the through-channels 3 filled up to an associated partial height i,j of the effective fill height g.

In an alternative variant, a reservoir 21 is provided containing a viscous or paste-like filler material 5 of higher viscosity. For example, the filler material has a viscosity in the range 104 to 106 mPa s. The filler material 5 is preferably selected for easy handling such that it is present on the support in a substantially static state at least temporarily while the support comprising the reservoir 21 is provided until insertion of the collimator walls. A specific example besides other options can include here, for instance, Scotch Weld DP 760 or Scotch Weld DP 490. The viscous or paste-like filler material 5 is applied, for instance, as a layer of specified and preferably constant layer thickness over the surface of a support. A doctor blade, for instance, can be used to apply the layer onto the support, for instance onto a pad.

The arrangement of the multiplicity of collimator walls can be pressed into the reservoir 21, whereby the viscous or paste-like filler material is introduced into the through-channels. As a result of the higher viscosity of the filler material 5, this can require a higher applied force than when immersing into a more free-flowing material of lower viscosity. For example, the arrangement of the collimator walls is pressed into the reservoir 21 until stopped by the support, with the filler material penetrating into the through-channels in the process. Then the support can be removed from the arrangement of collimator walls 1.

Figure 7:
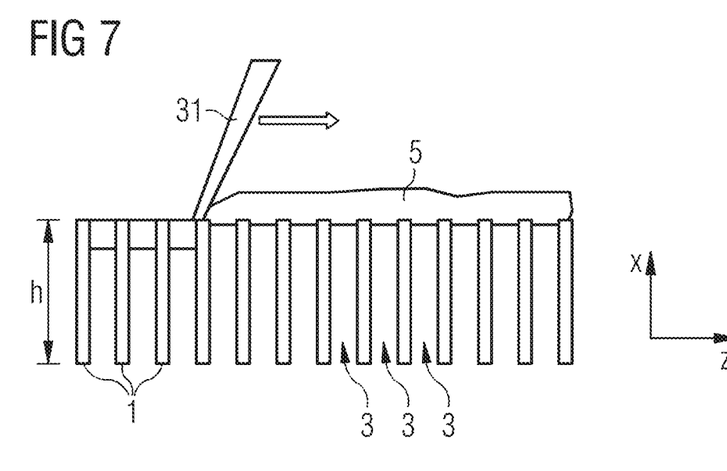
FIG. 7 is an illustration of a second embodiment variant of a method for producing an anti-scatter collimator.

FIG. 7 shows an illustration of a second embodiment variant of a method for producing an anti-scatter collimator 2.

In this variant, the step of at least partially filling S2 comprises applying the filler material 5 in a flowable or at least malleable state to the arrangement of collimator walls 1 arranged adjacently along a first direction, and introducing the filler material into the through-channels 3 by means of a mechanical process. The filler material 5 can then be hardened. The filler material is preferably in a viscous or paste-like state prior to the filling.

In the example shown, the preferably viscous or paste-like filler material 5 is applied in a layer thickness that is as uniform as possible over the surface of the beam exit side 8 and/or beam entry side 6 of the prepared arrangement of collimator walls 1, and introduced into the through-channels 3 by means of a doctor blade 31 by pulling or pushing (indicated by an arrow) the doctor blade over the arrangement of collimator walls, with the filler material 5 pressed into the through-channels 3 in the process. The filler material 5 preferably has a viscosity such that the filler material is present in a substantially static, i.e. non-flowing but deformable, state at least temporarily on the arrangement, and only applying a mechanical force results in filling of the through-channels 3. For example, the filler material has a viscosity in the range 104 to 106 mPa s. A specific example besides other options can include here, for instance, Scotch Weld DP 760 and materials with similar properties.

Adjusting the layer height of the layer applied to the arrangement also allows adjustment of the effective fill height in the through-channels 3. Likewise, reapplying a second layer and introducing the second layer into the through-channels 3 by the mechanical process can be used to achieve a greater effective fill height g.

Figure 8:
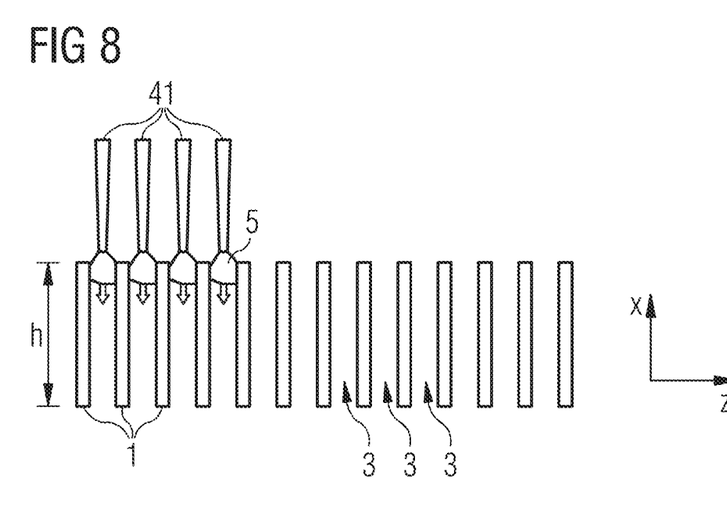
FIG. 8 is an illustration of a third embodiment variant of a method for producing an anti-scatter collimator.

FIG. 8 shows an illustration of a third embodiment variant of a method for producing an anti-scatter collimator 2.

In this variant, the step of at least partially filling S2 comprises using an application apparatus 41, for instance using cannulas or dispenser needles, to introduce the filler material 5 in a flowable or at least malleable state directly into the through-channels 3 individually. The filler material 5 can then be hardened. Individually means here that each through-channel 3 is filled separately successively in time by means of an application apparatus 41, for instance a cannula or dispenser needle, which can be positioned at a through-channel 3 or inserted into a through-channel 3, or that an application apparatus 41, for instance a cannula or dispenser needle, is provided for each through-channel 3 of at least one group of through-channels 3, and the through-channels in the group are filled simultaneously. The effective fill height g can then be determined by the amount of filler material 5 introduced into each through-channel 3. In this process, filling may comprise inserting the tip of a dispenser needle or cannula into a through-channel 3 and moving it out of the through-channel 3 as filler material 5 is discharged by the dispenser needle or cannula, leaving behind the discharged filler material 5 in the through-channel.

A higher viscosity (>103 mPa s) is again preferable in this case to prevent flow of the introduced material. For instance, the viscosity can be at least 104 mPa s. A specific example besides other options can include here, for instance, Scotch Weld DP 760.

Although the invention has been illustrated and described in detail with reference to the preferred example embodiments it is not limited hereby. A person skilled in the art can derive other variations and combinations herefrom without deviating from the fundamental idea of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An anti-scatter collimator for arranging in a stacked construction with an X-ray detector, the anti-scatter collimator having a beam exit side and a beam entry side, and the beam entry side being opposite the beam exit side in a direction of incidence of radiation, the anti-scatter collimator comprising:
   collimator walls arranged adjacently along at least a first direction, the collimator walls being mutually spaced to provide a plurality of through-channels, a through-channel among the plurality of through-channels being between each pair of adjacent collimator walls, and the plurality of through-channels being at least partially filled with a filler material,
   wherein the collimator walls include a wall height perpendicular to the first direction and in the direction of incidence of radiation,
   wherein an effective fill height of the filler material in the direction of incidence of radiation in the plurality of through-channels is less than the wall height of the collimator walls, and
   wherein the plurality of through-channels are filled with the filler material in a subregion adjoining the beam entry side.

2. The anti-scatter collimator of claim 1, wherein the filler material includes a hardenable filler material.

3. The anti-scatter collimator of claim 1, wherein the filler material includes an optically reflective material.

4. An X-ray detector apparatus, comprising:
an X-ray detector; and
the anti-scatter collimator of claim 1, the X-ray detector and the anti-scatter collimator being arranged in the stacked construction, and the anti-scatter collimator being arranged in front of the X-ray detector in the direction of incidence of radiation to reduce scattered radiation incident on the X-ray detector during illumination of the X-ray detector apparatus with X-ray radiation.

5. A medical imaging device, comprising:
the X-ray detector apparatus of claim 4; and
an X-ray source arranged opposite the X-ray detector apparatus, the X-ray source configured to illuminate the X-ray detector apparatus with the X-ray radiation for to produce X-ray image datasets.

6. A method for producing an anti-scatter collimator for arranging in a stacked construction with an X-ray detector, the anti-scatter collimator having a beam exit side and a beam entry side, and the beam entry side being opposite the beam exit side in a direction of incidence of radiation, the method comprising:
providing an arrangement of collimator walls, the collimator walls arranged adjacently along at least a first direction to provide a plurality of through-channels, a through-channel among the plurality of through-channels being between each pair of adjacent collimator walls;
at least partially filling the plurality of through-channels, provided by the arrangement of collimator walls, with a filler material, wherein
the collimator walls include a wall height perpendicular to the first direction and in the direction of incidence of radiation,
an effective fill height of the filler material in the direction of incidence of radiation in the plurality of through-channels is less than the wall height of the collimator walls, and
the plurality of through-channels are filled with the filler material in a subregion adjoining the beam entry side; and
hardening the filler material in the plurality of through-channels.

7. The method of claim 6, wherein the at least partially filling includes:
inserting the arrangement of collimator walls arranged adjacently along a first direction into a reservoir of filler material provided in a flowable or at least malleable state, to at least partially fill the plurality of through-channels.

8. The method of claim 6, wherein the at least partially filling includes using a vacuum process to at least partially fill the plurality of through-channels.

9. The method of claim 6, wherein the at least partially filling includes:
applying the filler material in a flowable or malleable state to the arrangement of collimator walls arranged adjacently along at least the first direction, and
introducing the filler material into the plurality of through-channels via a mechanical process to at least partially fill the plurality of through-channels.

10. The method of claim 6, wherein the at least partially filling includes:
using an application apparatus to introduce the filler material in a flowable or malleable state into the plurality of through-channels individually, to at least partially fill the plurality of through-channels.

11. The method of claim 7, wherein the at least partially filling includes using a vacuum process to at least partially fill the plurality of through-channels.

12. An X-ray detector apparatus, comprising:
an X-ray detector; and
the anti-scatter collimator of claim 2, the X-ray detector and the anti-scatter collimator being arranged in the stacked construction, and the anti-scatter collimator being arranged in front of the X-ray detector in the direction of incidence of radiation to reduce scattered radiation incident on the X-ray detector during illumination of the X-ray detector apparatus with X-ray radiation.

13. A medical imaging device, comprising:
the X-ray detector apparatus of claim 12; and
an X-ray source arranged opposite the X-ray detector apparatus, the X-ray source configured to illuminate the X-ray detector apparatus with the X-ray radiation to produce X-ray image datasets.

* * * * *